United States Patent [19]

Braden et al.

[11] 4,190,773
[45] Feb. 26, 1980

[54] SHUTTER FOR ROTATING SOURCE CT SCANNER

[76] Inventors: Arthur B. Braden, 6263 Gatewood Dr., Mentor, Ohio 44060; John J. Kuwik, 411 E. 322nd St., Willowick, Ohio 44094; Samuel K. Taylor, Taylor Wells Rd., Chardon, Ohio 44024; John Covic, 1581 Mapledale, Wickliffe, Ohio 44092

[21] Appl. No.: 812,317

[22] Filed: Jul. 1, 1977

[51] Int. Cl.² .......................... A61B 6/02; G01N 23/08
[52] U.S. Cl. .................................. 250/445 T; 250/505
[58] Field of Search ............................ 250/445 T, 505

[56] References Cited

U.S. PATENT DOCUMENTS

| | | | |
|---|---|---|---|
| 3,866,047 | 2/1975 | Hounsfield | 250/445 T |
| 4,097,747 | 6/1978 | Kowalski | 250/445 T |
| 4,132,895 | 1/1979 | Froggatt | 250/445 T |

*Primary Examiner*—Alfred E. Smith
*Assistant Examiner*—T. N. Grigsby
*Attorney, Agent, or Firm*—Faye & Sharpe

[57] ABSTRACT

In a CT scanner having a rotating source of radiation and a series of stationary radiation detectors spaced about the axis of rotation of the source, an eclipsing shutter mechanism restricts the width of the diverging fan pattern of radiation to that portion of the patient scan circle which is intermediate the array of stationary detectors and the orbiting source. The eclipsing shutter may include a single elongated slit aperture for flooding the scan circle with radiation or a plurality of smaller apertures defining a collimator for continuously training each one of a plurality of discrete diverging beams in the fan pattern on a single stationary detector during rotation of the source for as long as the separate beam intersects the scan circle. An epicyclic gear train powered by the rotation of the source drives the shutter mechanism in a counter-rotation and causes the collimator to keep each beam aimed at a respective detector.

51 Claims, 10 Drawing Figures

SHUTTER FOR ROTATING SOURCE CT SCANNER

BACKGROUND OF THE INVENTION

The invention relates generally to the field of radiation imaging of internal structures and, more specifically, to computerized transaxial tomographic (CT) X-ray scanners. Unlike conventional exposed film X-ray apparatus, the CT scanner produces narrow beams of radiation, either X-ray or gamma rays, through plural coplanar paths defining a cross-sectional or tomographic view of the patient's internal organs, such as the brain. The attenuated beams are sensed by radiation detectors whose electrical output is indicative of the intensity of the radiation received by the detector. One of the early types of CT scanners referred to in the patent literature is shown, for example, in Hounsfield U.S. Pat. No. 3,778,614. This system is generally referred to in the art as the "translate and rotate" system. A source and a single detector, for example, are aligned opposite each other on a mechanism which causes the beam path between the source and detector to move laterally across the scan circle. After rotating the source/detector carriage assembly to a new orientation, the translational scan is repeated. Readings are taken at uniformly spaced parallel beam locations and representative values are digitally stored. Data from a full set of scans involving numerous relocations of the beam path is manipulated according to known mathematics involving "back projection" to arrive at a digital representation of the tomographic image. This digital representation is converted to a tomogram which can be viewed on a cathode ray tube. Ohio-Nuclear, Inc. markets a type of translate and rotate CT scanner under the trademark "DELTA SCAN".

The major disadvantage of the translate and rotate system is slowness of the scan mechanism due to the different alternating types of motion. The major advantages of the translate and rotate system are due to the fact that a single detector scans across the entire scan circle thus enabling sampling at any time and avoiding the need to have matched detectors or gain matching.

Another type of scan technique called "purely rotational" employs a fan beam source with a subtended detector array in a fixed relationship such that the fan beam and detector array rotate with each other. This system has a major disadvantage. Numerous detectors are required and none scans across the entire patient. Thus, the sampling resolution is lowered and gain matching of the detectors is required. The major advantage of the purely rotational system is its high scanning speed. The high speed of the scanning motion is desirable to avoid the effect on the image of the resultant displacement of organs due to a patient's breathing.

It has been found that computer image reconstruction can be accomplished with yet another arrangement of source and detectors. In this new system, the detector array is a stationary arc of uniformly spaced detectors about the center point in the scan circle. The fan pattern source revolves about the center point inside the detector array irradiating the scan circle and subtending at any given time only a fraction of the detectors in the total array. If desired, the array may be a complete circle or ring. The reconstruction algorithms are described in Lakshminarayanan, "Reconstruction from Divergent Ray Data", Technical Report No. 92, State University of New York at Buffalo, Computer Sciences Department, January 1975.

The new type of scanning system, although requiring numerous detectors and somewhat more elaborate digital processing for reconstructing an image, provides the advantage of high scanning speed due to the single mechanical motion for rotation while also providing the capability of achieving high sampling resolution and avoiding gain matching requirements because each detector views the source across the entire scan circle.

If the circular array of detectors does not fully encircle the patient, it is possible for the patient to be exposed to unused radiation when the source approaches the terminus of its orbit and part of the fan pattern falls outside the detector array. Another problem is presented when the detectors are spaced apart throughout the array since the fan pattern is not aligned with specific detectors but instead floods the scan circle. In this case, a portion of the radiation falls between adjacent detectors and is not used for data collection. This radiation dosage is received by the patient, however, even though it is not used.

SUMMARY OF THE INVENTION

The purpose of the invention is to reduce the dosage of unused radiation which the patient receives when a rotating source is used with a series of stationary detectors in a CT scanner system. This is accomplished by employing an eclipsing shutter mechanism to limit the portion of the fan pattern of radiation passing through the scan circle at all times to a width coincident with the subtended portion of the detector array. When the detectors are sufficiently spaced apart in the detector array, unnecessary dosage is reduced by dividing the fan pattern into a plurality of discrete diverging beams and keeping them trained on respective detectors for as long as they are within the scan circle.

The CT scanner arrangement to which the invention applies is one in which the source rotates and a series of detectors is spaced about the center of rotation coplanar with the orbit of the source. A radiation shield restricts the radiation from the source to a solid fan pattern centered on the axis of rotation. An eclipsing shutter mechanism about the source restricts the fan pattern at all times to a pattern which will fall on the detector array as the source traverses its orbital path. The shutter mechanism may include a single aperture for flooding the scan circle or a multi-apertured collimator, with one aperture for each detector, for training each one of the discrete beams collectively defining the fan pattern on a specific detector for as long as each beam intersects the scan circle. The shutter mechanism is responsive to rotation of the source which causes a specific fractional amount of rotation in the opposite direction as the source moves. When the collimator is employed the respective apertures keep themselves aligned between the source and their respective detectors through the scan circle. In the preferred embodiment, the means for rotating the shutter mechanism is an epicyclic gear train, although other means are possible such as a d. c. motor servo drive, or the like.

DESCRIPTION OF THE PREFERRED EMBODIMENTS

Figure 1:
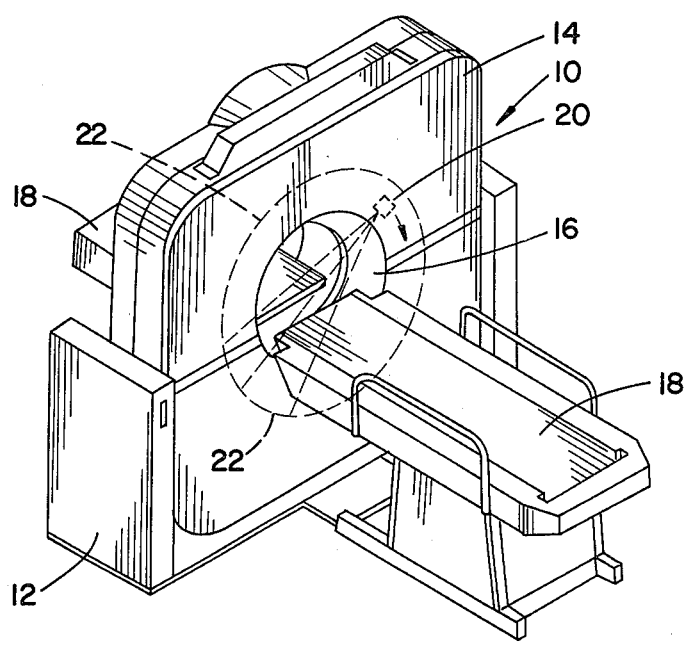
FIG. 1 is a perspective view of CT scanner apparatus associated with the invention.

FIG. 1 illustrates the mechanical apparatus associated with the rotation source type CT scanner system. A gantry assembly 10 includes a U-shaped frame 12 pivotally supporting a gantry 14 having a central circular opening 16 through which a patient is inserted for a body scan, for example, on a two-piece patient table 18. Shown in phantom, the source 20 produces radiation in a coplanar fan pattern directed towards the opposite side of the opening 16 and intersecting the center of the opening 16. Mechanisms within the gantry 14 rotate the source 20 clockwise about an axis through the center of the opening 16 perpendicular to the fan pattern. A ring of detectors 22, also shown in phantom in FIG. 1 is disposed within the gantry 14 concentrically to the opening 16 and at a somewhat greater radius from the center of the opening 16 than the source 20. The detector ring 22 lies in the same plane as the fan pattern. The signals produced by detectors which are within the fan pattern are applied to a number of respective signal processing channels. By using the multiplexing system described in the copending application Ser. No. 783,732, entitled "Data Multiplexing System for CT Scanner with a Rotating Source", filed Apr. 1, 1977 and assigned to the assignee of the present application, the number of signal processing channels can be reduced to the maximum number of detectors subtended by the fan pattern and the detectors can time share these signal processing channels. The copending application is incorporated by reference herein.

Figure 2:
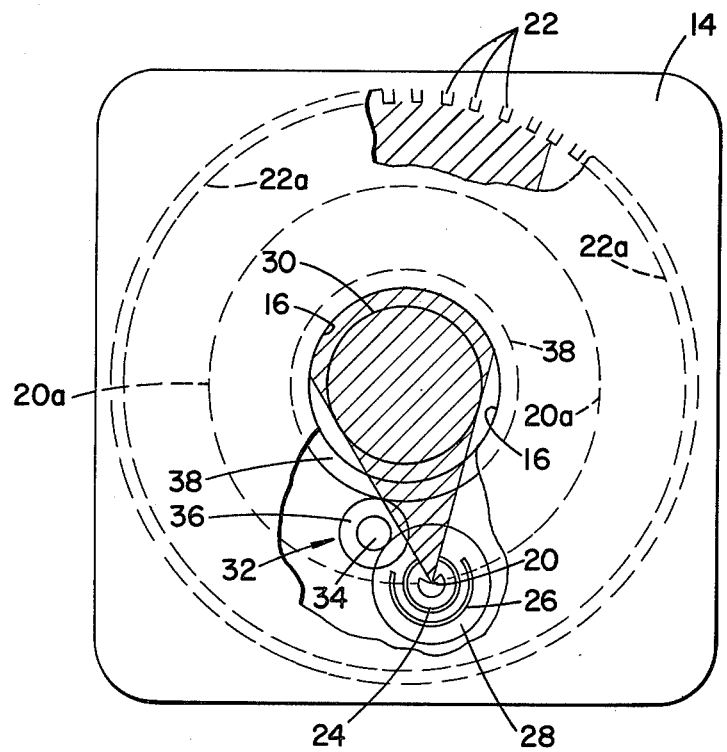
FIG. 2 is a plan view of the gantry with portions broken away to expose the epicyclic gear train driving the shutter mechanism.

In FIG. 2, the view of the gantry 14 shows the source 20 at a low point on its orbit through circular path 20a. The source 20 lies within a radiation shield 24 having a sector missing which causes the radiation directed toward the opening 16 to assume a fan shape. The thickness of the fan in the direction orthogonal to the paper is slightly divergent and at the center of rotation represents the thickness of the slice or tomogram to be reconstructed. Between the source 20 and the opening 16 a shutter mechanism 26 having either a single aperture or a series of very closely spaced apertures concentric to the source 20 is mounted for rotation on a planetary gear 28 rotatable upon an axis coinciding with the source 20.

The source 20 with shield 24 produces a fan pattern of radiation whose angular width determines the diameter of a patient scan circle 30 at a given distance from the center of the scan circle. The scan circle 30 includes the area common to the fan at different positions of the source 20 along its orbit 20a. The area within the scan circle is the area which the reconstructed image will represent. Thus, this area will coincide with the portion of the patient's body, for example, the head.

The angular size of the single aperture 26a (FIGS. 4–6) in the shutter mechanism 26 is dependent upon the number and spacing of detectors 22. However, the arc spanned by the aperture 26a in the shutter mechanism is less than the arc spanned by the array of detectors 22. For example, if there are 424 detectors with half-degree spacing from the center line of one detector to the center line of the next detector, they cover an arc of 211° on the detector ring 22a. In the embodiment illustrated in FIGS. 2–6, the resulting arc spanned by aperture 26a in the shutter mechanism is only 127.2°, i.e., 60% of the arc spanned by the detector array.

Figure 3:
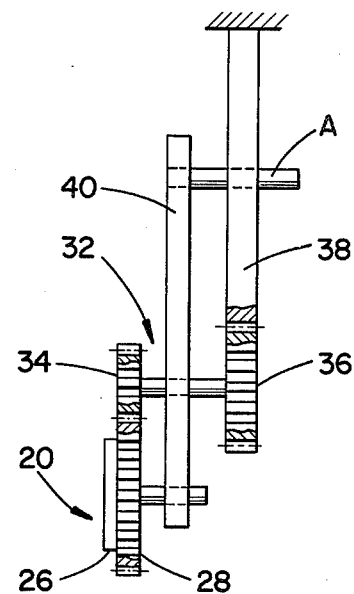
FIG. 3 is a side schematic detail view of the epicyclic gear train.

With reference to FIGS. 2 and 3, a compound gear 32 is used to drive the planetary gear 28 on which the source 20, fan shield 24 and shutter 26 are arranged. Compound gear 32 includes a smaller spur gear 34 driving the planetary gear 28 and a larger spur gear 36, connected for rotation with smaller gear 34, engaging a stationary ring-shaped sun gear 38 affixed to the gantry and concentric with the scan circle about center c. As the source 20 orbits in a clockwise direction along its path 20a, the compound drive gear 32 is caused to rotate clockwise which in turn causes the planetary gear 28 and shutter 26 to rotate counterclockwise. As shown in FIG. 3 in schematic form the axes of the gears are all fixed with respect to each other. For purposes of illustration, this is indicated by arm 40 of FIG. 3 to which the imaginary axle A of the sun gear 38 coinciding with the center c of the scan circle is journalled along with the common axle of the compound gear 32 and the axle of the planetary gear 28. Since the sun gear is fixed, the arm 40 is free to rotate about the imaginary axle A. This rotation produces the orbit of the source 20 with shield 24. This motion is analogous to a solar, planet and moon system in which the sun gear 38 represents the sun, the source 20 represents the earth and a fixed point on the planetary gear 28, for instance, the aperture in the shutter mechanism 26 represents the moon.

Figure 4:
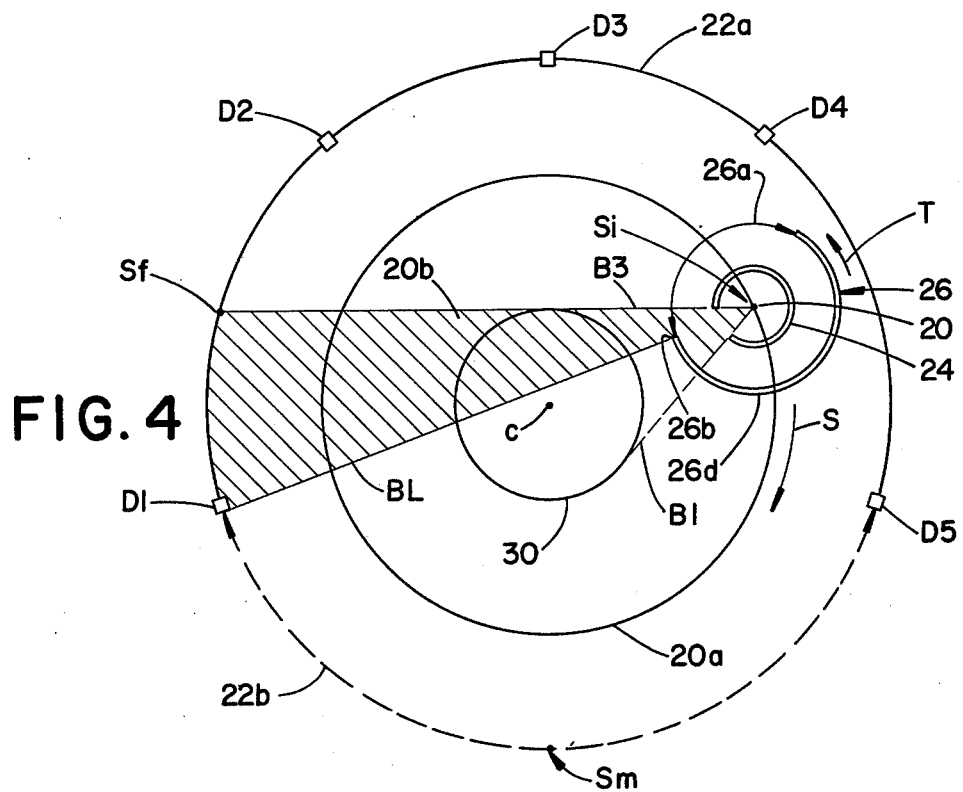
FIGS. 4, 5 and 6 are schematic representations of the relative positions of the source, shutter mechanism, resulting fan pattern and detectors at three different orientations.
Figure 5:
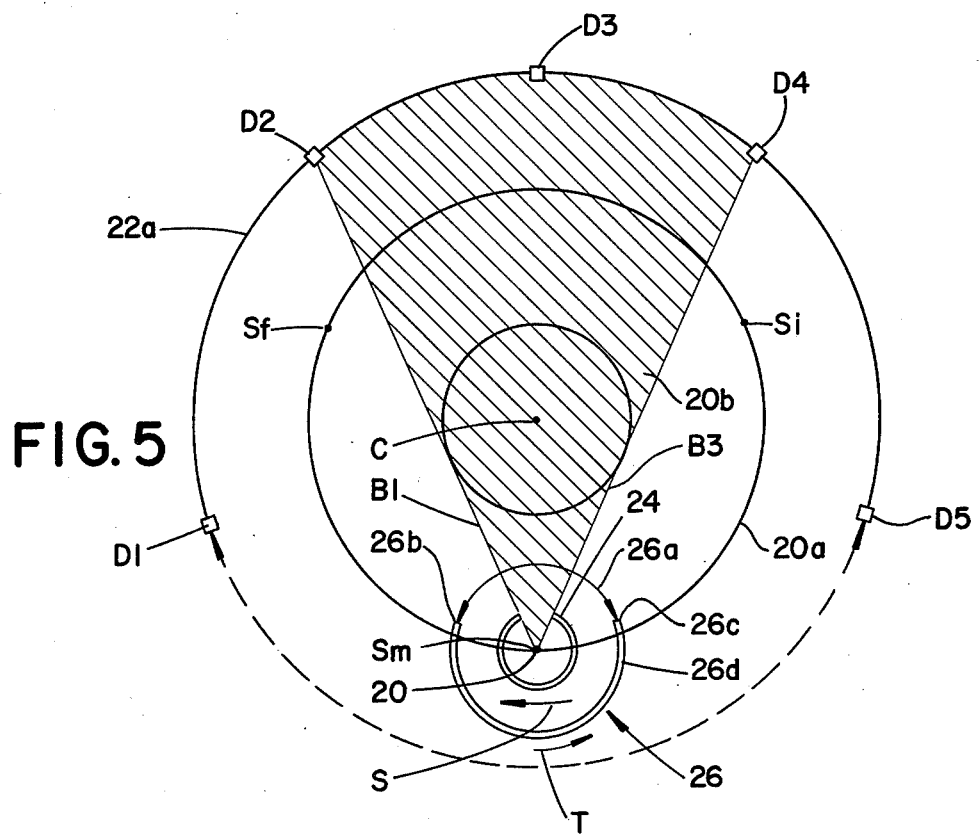
Figure 6:
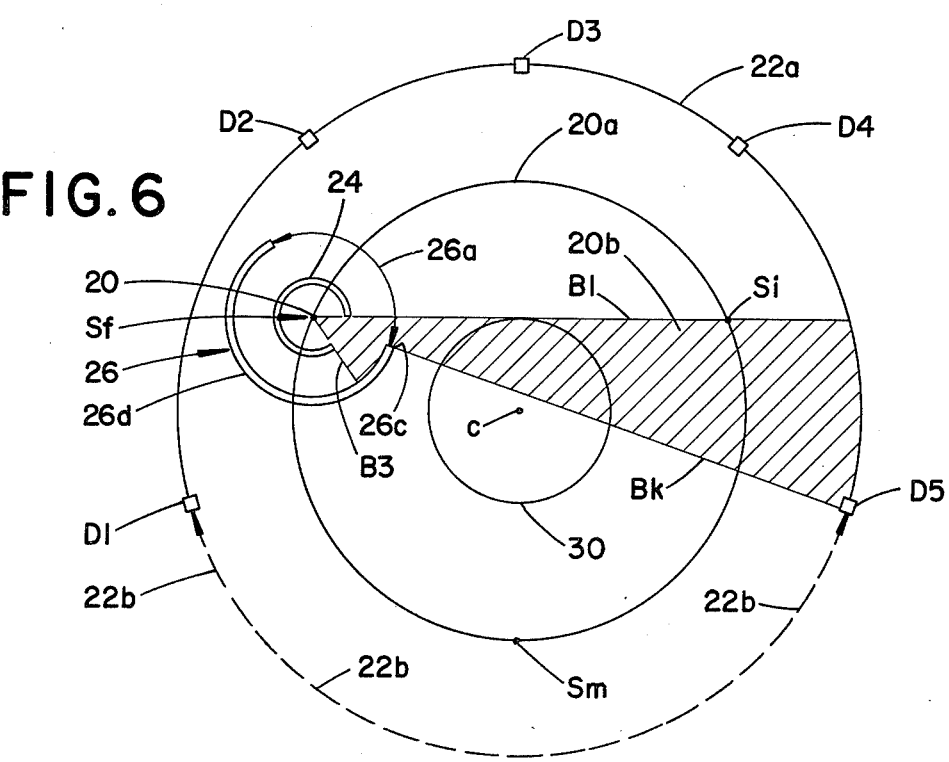
Figure 7:
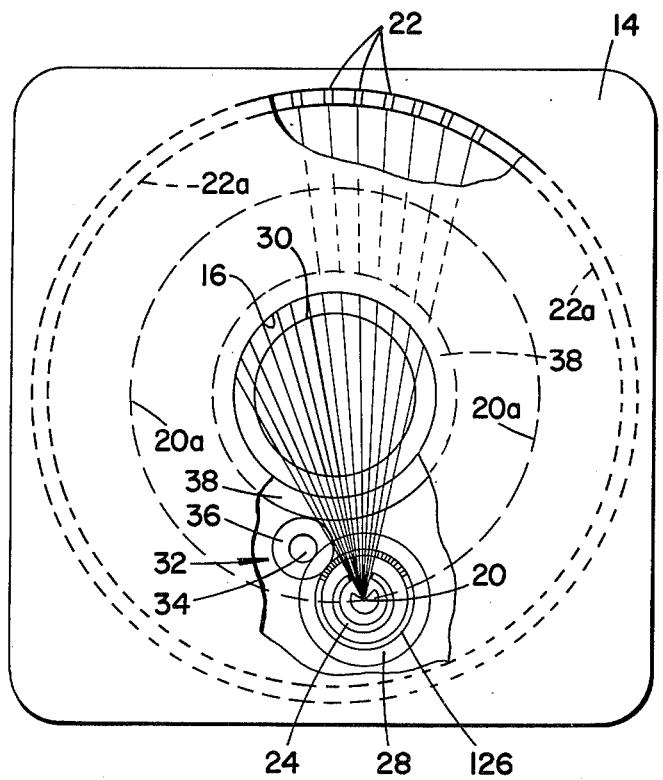
FIG. 7 is a plan view, similar to FIG. 2, showing a shutter mechanism having a multi-apertured collimator and the resulting discrete, diverging beams of the fan pattern.

The requirement for this type of motion between the shutter mechanism and the source is demonstrated in FIGS. 4, 5 and 6 showing progressive clockwise orientations of the source. In FIG. 4, the source is shown at the initial point $S_i$ of the scan cycle. In FIGS. 5 and 6, the source is shown at the midpoint $S_m$ of the scan cycle and at the final or end-point $S_f$ of the scan cycle, respectively. FIGS. 4, 5 and 6 also show detector ring 22 and, for illustration, the first, last and three intermediate stationary detectors D1, D2, D3, D4 and D5 in the ring. Of course, in the practical embodiment there are many detectors in the spaces between detectors D1–D5. The arc 22a is bounded by detectors D1 and D5 and defines the detector array span. Arc 22b is that portion of the detector ring which is outside the detector array.

In FIG. 5, the source 20, with shield 24, produces an X-ray field defined by the fan pattern 20b having outer, diverging boundaries B1 and B3 which define the included angle of the fan pattern which floods the scan circle 30. As shown in FIGS. 4 and 6, the eclipsing shutter mechanism 26 acts to reduce the included angle of fan pattern 20b whenever the source approaches either terminus $S_i$ or $S_f$ of its cycle. This is desirable because the array of detectors on ring 22 does not entirely encircle the scan circle and if the width of the radiation field was not so restricted, unused radiation would pass through scan circle 30 and needlessly increase the patient dosage.

The eclipsing effect of the shutter 26 is accomplished by utilizing the epicyclic mechanism of FIG. 3. It should, of course, be understood that other drive mechanisms such as, by way of example, a d. c. motor servo drive may also be employed. In the illustrated embodiment, the included angle between the first detector D1 and the last detector D5 is 211°. The remaining arc 22b of ring 22, 148° in the example, is outside the detector array. The shutter mechanism 26 is utilized to preclude the projection of any portion of the X-ray of fan pattern 20b through the scan circle if that portion of the field would fall outside the detector array, i.e., on arc 22b.

With the arrangement shown in the drawings, a 60% rotation of shutter 26 is required for each 100% positive rotation of source 20 about its orbital path 20a. The source moves from point $S_i$ to point $S_f$ on path 20a in the direction of arrow S during a scan cycle, and the shutter rotates in the opposite or negative direction as indicated by arrow T. As shown in FIG. 4, the leading edge 26b of the shutter aperture is on a straight line projecting from detector D1 to source 20 for as long as a straight line projecting from detector D1 to the source intersects the scan circle 30. Thus, the shutter imposed boundary $B_L$ of fan pattern 20b is trained on detector D1 continuously for as long as the detector is in the data-taking portion of the scan cycle. There may be some minor deviation of the imposed boundary $B_L$, which is in effect the same as the deviation of an individual slit in the rotating collimator described below. The portion of the fan pattern between the trailing edge B1 of the fan pattern and the shutter imposed boundary $B_L$ is blocked by the shielding portion 26d of shutter 26 and does not pass through the scan circle 30. This is desirable since this portion of the fan pattern would fall outside the detector array and would needlessly increase the patient's exposure to radiation.

As the source traverses about its orbital path 20a in the direction of arrow S (clockwise), the shutter 26 rotates in the direction indicated by arrow T (counterclockwise) 0.6° for every 1° of source rotation, ever increasing the fan pattern width while continuously training the shutter imposed boundary $B_L$ of the fan beam on the detector D1 for as long as the detector D1 is in the data-taking portion of the cycle, i.e., the scan circle is intermediate the detector D1 and the source 20. The fan pattern continues to widen until the entire fan pattern bounded by leading edge B3 and trailing edge B1 falls on the detector array. At this point, the shutter aperture is completely out of the path of the fan pattern emanating from source 20 and the entire fan pattern floods the patient scan circle 30. This is desirable since the entire fan pattern falls on the detector array.

The source 20 is shown at the mid-point $S_m$ of its travel in FIG. 5. This is representative of the flooded scan circle wherein the leading edge B3 of the fan pattern 20B falls on detector D2 and the trailing edge B1 falls on detector D4. As the source 20 continues its movement, leading edge B3 of the fan pattern approaches detector D5, the last detector in the array. Again, it is desirable to block any portion of the fan pattern which will fall outside the detector array span. At this point, illustrated in FIG. 6, trailing edge 26c of the shutter aperture has rotated into blocking relationship with the source and shields the leading edge B3 and a portion of the fan pattern 20B, training the shutter imposed boundary $B_K$ on the last detector D5 for as long as the detector D5 is in the data-taking portion of the scan cycle. After the source has completed its orbital cycle by traversing to point $S_f$, both the source and the shutter are returned to the initial position $S_i$ of FIG. 4.

By utilizing the shutter mechanism 26, the source can be rotated through any portion of its orbital path without passing any radiation through the scan circle that does not ultimately fall on the detector array span. The single apertured shutter mechanism 26 of FIGS. 1-6 is practical whenever the detectors in the detector array are spaced in such a manner that it is desirable to flood the scan circle with radiation. In the preferred embodiment, this system has been utilized, for example, when the center line of adjacent detectors are at approximately one-half degree spacing. When the detectors are more widely spaced about ring 22, it is possible to further reduce the patient dosage by subdividing the fan pattern into a plurality of discrete beams, each trained on a particular detector for as long as the detector is in the data-taking portion of the scan cycle.

The beam subdivision is accomplished by replacing the single-apertured shutter 26 with a multi-apertured shutter or collimator 126 as shown in FIGS. 7-10. The first and last apertures in the rotating collimator effectively perform the same function as the trailing and leading edge of the eclipsing shutter. The number of apertures in the collimator 126 corresponds to the number of detectors 22. However, as with the single-apertured shutter 26, the arc spanned by the apertures in the collimator 126 is less than the arc spanned by the detectors 22. For example, if there are 212 detectors with 1° spacing from the center line of one detector to the center line of the next detector, they cover an arc of 211° on detector ring 22a. There would be 212 closely machined apertures in the collimator 126, one for each detector. However, as with the shutter aperture 26a, the arc spanned by the 212 apertures is again only 127.2°, i.e., 60% of the arc spanned by the detector array in the embodiment illustrated.

The apertures in the collimator 126 make a plurality of narrow discrete diverging equally, angularly spaced beams which collectively form the fan pattern 20b whose angular width at a given distance from a scan center determines the diameter of the patient's scan circle 30. The object of the collimator 126 is to keep each beam of fan pattern 20b aimed toward a specific single detector while the source 20 moves along the path 20a. Of course, this is only of importance while the line between the particular detector and the source intersects the scan circle 30. The line will intersect the scan circle over the angle defined as the "detector angle" subtended from the detector by the diameter of the scan circle.

Figure 8:
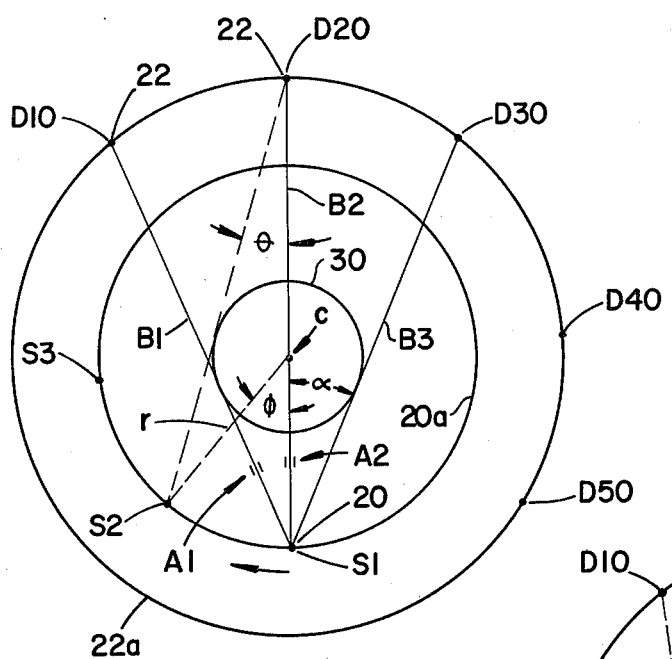
FIGS. 8, 9 and 10 are schematic representations of the relative positions of the source, collimated beams and detectors at three different orientations.
Figure 9:
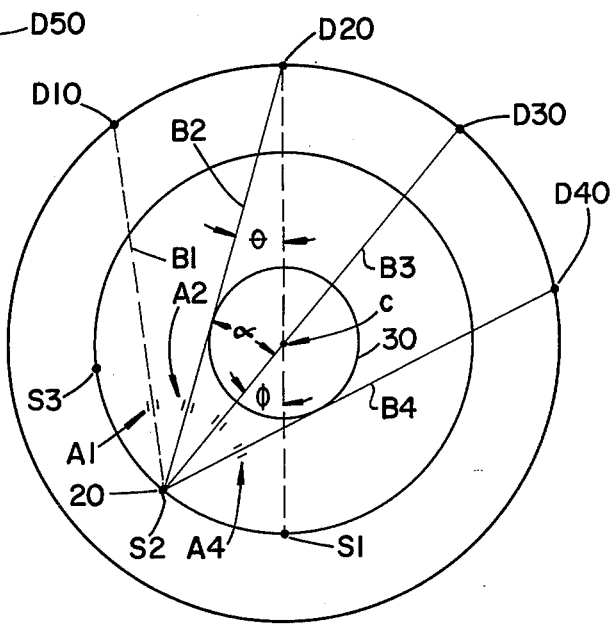
Figure 10:
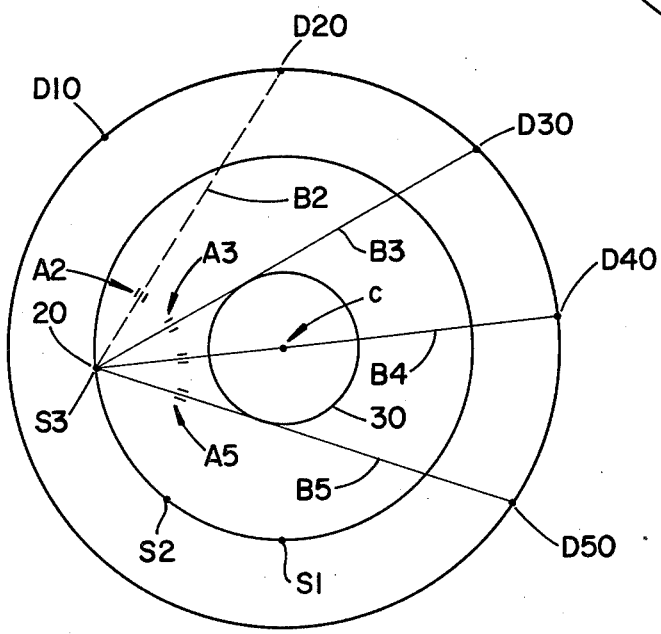

The epicyclic motion between the collimator ring and the source is demonstrated in FIGS. 8, 9 and 10 showing progressive clockwise orientations of the source separated by 40°. FIG. 8 shows three successive source positions S1, S2 and S3 each separated by 40° as the source traverses orbit 20a in the clockwise direction. FIG. 8 also shows detector ring 22 and, for illustration, five stationary detectors D10, D20, D30, D40 and D50. Source 20 produces a fan of plural diverging beams centered collectively on the center c of rotation of the source 20. Three of these plural beams B1, B2 and B3 have been selected for FIG. 8 because of their geometric significance. As in FIGS. 4-6, beams B1 and B3 are the peripheral beams of of the fan beam pattern and are tangent to the scan circle 30. Beam B2 passes through the center c. The fan beam width is twice α, where α is the angle made by beams B2 and B3. In practice, there are many beams between B1 and B2 and B2 and B3. Likewise, there are many detectors between each one of the five detectors shown in FIG. 8. Detector D10 is defined as the detector lying on the tangent from the source position S1. Detector D20 is aligned with the center and position S1 and detector D30 lies on the other tangent to the scan circle from position S1.

In FIG. 8, beam B2 is defined by aperture A2, one of the apertures in the collimator ring 26 of FIG. 2. In this orientation, the aperture A2 sights the source along the center c. As the source 20 moves from position S1 to S2, it moves through the angle $\phi$ about the center c of rotation. The radius r from the new source position S2 to center c in FIG. 8 indicates the direction in which the aperture A2 would aim the source if aperture A2 were fixed to the source and thus always looking toward the center c. This would mean that beam B2 would no longer be looking at detector D20 but would be looking in the direction of detector D30. While the source is moving from position S1 to S2, it is not desirable for the beam B2 to move its target along the path from D20 to D30. Instead, beam B2 should be continuously trained on detector D20 as shown in FIG. 9. This requirement dictates that aperture A2 will not be aligned with the radius but rotate through the angle $\alpha$ to a new angular orientation about the source 20 such that the beam B2 remains directed at detector D20. While the source is moving from S1 to S2 through angle $\phi$, the aperture A2 must be moving continuously through an angle which grows to angle $\alpha$ at the same time. This means that the aperture A2 has to rotate counterclockwise about the source 20 as the source 20 moves clockwise from position S1 to position S2 in order to keep beam B2 trained on detector D20.

Aperture A2 represents but one of the apertures for the many detectors between detector position D10 and detector position D30 in the practical embodiment. All of the beams have to be slued or scanned across the scan circle in the same manner as B2. For example, beam B3 has just come into being, that is, has just intersected the scan circle 30 and for the first time detector D30 is illuminated by radiation from B3. As the source 20 moves from position S1 to S2, beam B3 remains trained on the detector D30 as shown in FIG. 9. The only way that this can be accomplished is for its corresponding aperture A3 to rotate the same amount and sense or direction as aperture A2. Thus, in FIG. 9, beam B3 views detector D30 through the center c although before in FIG. 8, beam B3 started out on the periphery of the scan circle 30. At the time shown in FIG. 8 detector D10 is at the point where it is about to lose communication with the radiation fan altogether. Beam B1 has been slued all the way across the scan circle 30 to its periphery and as the source begins to move clockwise from position S1 even slightly, the beam B1 trained on detector D10 by corresponding rotating aperture A3 falls outside of the scan circle 30 and is darkened by the fan shield 24 shown in FIG. 2. Thus, the beam B1 shown in FIG. 9 after the source has moved to position S2 is only imaginary since it is blocked by the shield 24. The only active beams in FIG. 9 are those beams B2, B3 and new beam B4 which has just become tangent for the first time with the scan circle 30. Aperture A4 trains beam B4 on detector D40.

In FIG. 10, after the source 20 has moved through another 40° clockwise to position S3, beams B1 and B2 are no longer in use and new beam B5 trained on detector D50 through aperture A5 has come into view, tangent to the scan circle 30. By the time shown in FIG. 10, beam B3, which came into view for the first time in position S1 in FIG. 8, has been slued through the center c of the scan circle 30 in FIG. 9 and is now tangent for the last time to the scan circle 30 just before it will pass out of view. The aperture A2 which was originally centered on the center c in FIG. 8 has by the time the source has moved through 80° in FIG. 10 moved around the source S3 so far that it is no longer even sighting the source through the scan circle.

It is important to note that the angle through which aperture A2 has moved is not 80°; it is less than 80° because of the geometry of the source and detector arrangement. The ratio of the angular velocity of the source to the angular velocity of the aperture A2 or any other aperture on the collimator (or the single aperture 26a of FIGS. 1-6) is determined by the relationship between the radius of the source orbit and the radius of the detector ring. It can be shown that there are values for these two radii at which the ratio of the angular velocities of the source about the center c and the collimator ring (or shutter 26 in FIGS. 1-6) about the source 20 are rational numbers which can be accommodated by a reduction gear train. For example, it can be shown that if the detector ring has a radius of 36" and the source has a radius of 24.3", the angular velocity of the collimator (or shutter in FIGS. 1-6) around the source 20 should be exactly 60% (in the opposite direction) of the angular velocity of the source 20 about the center c. This ratio (−0.60) is relatively amenable to a toothed gear train solution.

It can also be shown that if the detector ring is kept at 36" and the source is moved from 24.3 to 24.0" that the angular velocity ratio becomes −0.603015. This ratio cannot be practicably resolved with a simple gear train. Although it is true that a friction drive of appropriately sized wheels might accommodate such a ratio, the dimensional instabilities in a friction drive assembly make it appear to be inappropriate for accurate registration of the collimator assembly. Toothed gears on the other hand are extremely accurate because there is no slippage allowed. This same relationship holds true when the single apertured shutter 26 of FIGS. 1-6 is utilized.

There is another anomalous factor at work in the geometry of FIGS. 8-10. Even with the "best" angular velocity ratio, namely 0.603015 for a source location of 24.0", the beams do not tract the detectors perfectly, that is, there is a slight aberration or error as the source orbits. The center line of a given beam, although aimed in the direction of a particular detector, will travel slightly over the center line of the detector.

There is another reason why the location of the source at 24.0" would have been undesirable. A very minor change in the source location from 24.0" to 24.3" not only caused the angular velocity ratio to become a rational number (−0.6000) but also at the same time it reduced the error of the beam tracking to within a range of plus or minus 1.037 to 1.078 millimeters. This tracking linearity error was calculated for the condition where the X-ray beam is emitted through particular aperture over approximately 80° of source rotation, the full angle in FIG. 8 through which each beam is slued through the scan circle 30.

These dimensions are, in fact, used for the preferred embodiment, a commercial model of which is under development by the assignee. Thus, with the source orbit at 24.3" and the center of each detector face at 36.0", the ratio of −0.60 for the angular velocities of the source and collimator or shutter is accomplished by the following gears, referring to FIG. 3: the sun gear 38 has 600 teeth; the larger compound gear 36 engaging the sun gear 38 has 100 teeth; the smaller compound gear 34 engaging the planetary gear 28 has 40 teeth and the planetary gear 28 has 400 teeth. The ratio of the number of teeth on the sun gear 38 to the number of teeth on the larger compound gear 36 multiplied by the ratio of the number of teeth on the smaller compound gear 34 to the number of teeth on the planetary gear 28 is 0.600. Any other kind of epicyclic gear train that reverses the sense of rotation of the planetary gear and collimator ring 26, and provides a reduction of exactly 60% will do. It also appears, because of the circular geometry of the system, that the dimensions of the radii of the source and detector ring will scale properly; that is, the ratio of the detector ring radius to the source radius, 1.48, for the preferred embodiment, will require an angular velocity ratio for the collimator and source of exactly 60% no matter what the size of the system.

This invention has been described with reference to the preferred embodiments with some possible modifications thereto. Obviously, other modifications and alterations will be obvious to others upon the reading and understanding of this specification. It is our intention to include all such modifications and alterations insofar as they come within the scope of the appended claims or the equivalents thereof.

The invention claimed is:

1. A shutter mechanism for a CT scanner having a rotating source of radiation and a series of stationary radiation detectors coplanar with the path of the source and spaced about the axis of rotation of the source and partially encircling the path of the source, defining a detector array, comprising:
   means for restricting radiation emitted from the source to a diverging fan beam centered on the axis of rotation;
   the common area within the angle of the fan beam at different positions of the source defining a patient scan circle; and
   adaptive aperture means between the scan circle and the source for limiting the radiation which passes through the scan circle to a pattern which falls on the detector array for all positions of the source.

2. The mechanism of claim 1, wherein said aperture means includes an apertured body at least partially encircling the source in the plane of the detectors and rotatable about the source.

3. The mechanism of claim 2, wherein said apertured body has a radiation passing section subtending an angle from the source coplanar with the detectors, having a predetermined proportion to the arc spanned by all the detectors.

4. The mechanism of claim 3, wherein said aperture means further includes means for causing a fixed amount of rotation of said apertured body in the opposite sense about the source for each angular unit of rotation of the source.

5. The mechanism of claim 4, wherein the angle of the radiation passing section is in the same proportion to the detector arc as said fixed amount of rotation is to said angular unit of rotation of the source.

6. The mechanism of claim 5, wherein said means for causing a fixed amount of rotation is a mechanical drive system powered by rotation of the source and connected to rotate said body.

7. The mechanism of claim 6, wherein said drive system is a set of wheels making driving contact with each other.

8. The mechanism of claim 7, wherein said wheels are gears.

9. The mechanism of claim 8, wherein said gears comprise an epicyclic gear train providing a gear reduction ratio of 1 to $-0.60$ of the source rotation to the rotation of the apertured body about the source.

10. The mechanism of claim 9, wherein the detectors are all the same distance from the center of the scan circle 1.48 times the radius of the source path.

11. The mechanism of claim 10, wherein the source is located at a distance of 24.3″ from the center and the detectors are located 36″ from the center.

12. The mechanism of claim 8, wherein said gears comprise an epicyclic gear grain.

13. The mechanism of claim 12, wherein said epicyclic gear train includes a planetary gear concentric with said source and moving therewith to which said apertured body is fixed, a stationary ring-shaped sun gear concentric to the scan circle, a compound drive gear consisting of a first gear engaging the sun gear and a second gear fixed to the first gear engaging the planetary gear.

14. The mechanism of claim 13, wherein said epicyclic gear train provides a gear reduction ratio of 1 to $-0.60$ of the source rotation to the rotation of said apertured body about the source.

15. The mechanism of claim 14, wherein the ratio of the number of teeth on the sun gear to the number of teeth on the first compound gear multiplied by the ratio of the number of teeth on the second compound gear to the number of teeth on the planetary gear is 0.60.

16. The mechanism of claim 5, wherein said radiation passing section has a single continuous aperture coextensive with said angle of said radiation passing section.

17. The mechanism of claim 1, wherein said aperture means includes:
   collimator means for restricting the radiation in said fan beam to a plurality of diverging separate beams; and
   means for continuously training each one of said separate beams on a single stationary detector during rotation of the source for as long as the separate beam intersects the scan circle.

18. The mechanism of claim 17, wherein said training means includes means for causing a fixed amount of rotation of each separate beam in the opposite sense about the center of the source for each angular unit of rotation of the source.

19. The mechanism of claim 17, wherein said aperture means is a collimator body rotatable about the source having a plurality of radiation apertures coplanar with the detectors spaced about the source.

20. The mechanism of claim 19, wherein said training means includes means for causing a fixed amount of rotation of said collimator body in the opposite sense for each angular unit of rotation of the source.

21. The mechanism of claim 20, wherein the arc spanned by all of said apertures is in the same proportion to the arc spanned by all the detectors as said fixed amount of rotation of each separate beam is to said angular unit of rotation of said source.

22. The mechanism of claim 21, wherein said means for causing a fixed amount of rotation is a mechanical drive system powered by rotation of the source and connected to rotate said body.

23. The mechanism of claim 22, wherein said drive system is a set of wheels making driving contact with each other.

24. The mechanism of claim 23, wherein said wheels are gears.

25. The mechanism of claim 24, wherein said gears comprise an epicyclic gear train providing a gear reduction ratio of 1 to −0.60 of the source rotation to the rotation of the collimator body about the source.

26. The mechanism of claim 25, wherein the detectors are all the same distance from the center of the scan circle 1.48 times the radius of the source path.

27. The mechanism of claim 26, wherein the source is located at a distance of 24.3" from the center and the detectors are located 36.0" from the center.

28. The mechanism of claim 24, wherein said gears comprise an epicyclic gear train including a planetary gear concentric with said source and moving therewith to which the collimator body is fixed, a stationary ring-shaped sun gear concentric to the scan circle, a compound drive gear consisting of a first gear engaging the sun gear and a second gear fixed to the first gear engaging the planetary gear.

29. The system of claim 28, wherein said epicyclic gear train provides a gear reduction ratio of 1 to −0.60 of the source rotation to the collimator body rotation about the source.

30. The system of claim 29, wherein the ratio of the number of teeth on the sun gear to the number of teeth on the first compound gear multiplied by the ratio of the number of teeth on the second compound gear to the number of teeth on the planetary gear is 0.60.

31. The mechanism of claim 1, wherein said aperture means includes means for blocking only the portion of said fan beam falling outside the arc spanned by the detectors for all positions of the source.

32. An adaptive radiation aperture system for a CT scanner having a rotating source of radiation and a detector array including a series of stationary radiation detectors coplanar with the path of the source and spaced about the axis of rotation of the source at least partially encircling the path of the source, comprising:
  means for restricting radiation emitted from the source to a diverging inwardly directed fan beam;
  a radiation blocking body having at least one radiation passing aperture between the source and its axis of rotation mounted for rotation about the source; and
  mechanical drive means for causing a fixed amount of rotation of said body in the opposite sense about the source for each angular unit of rotation of the source.

33. The system of claim 32, wherein said mechanical drive means is powered by the rotation of the source.

34. The system of claim 33, wherein said mechanical drive means includes a set of wheels making driving contact with each other.

35. The system of claim 34, wherein said wheels are gears.

36. The system of claim 35, wherein said set of wheels include an epicyclic gear train having a planetary gear concentric with said source and moving therewith to which said body is fixed, a stationary ring-shaped sun gear concentric to the scan circle, a compound drive gear consisting of a first gear engaging the sun gear and a second gear fixed to the first gear engaging the planetary gear.

37. The system of claim 36, wherein said epicyclic gear train provides a gear reduction ratio of 1 to −0.60 of the source rotation to the rotation of said body about the source.

38. The system of claim 36, wherein the ratio of the number of teeth on the sun gear to the number of teeth on the first compound gear multiplied by the ratio of the number of teeth on the second compound gear to the number of teeth on the planetary gear is 0.60.

39. The system of claim 38, wherein the detectors are all the same distance from the center of the scan circle 1.48 times the radius of the source path.

40. The system of claim 39, wherein the source is located at a distance of 24.3" from the center and the detectors are located 36.0" from the center.

41. A radiation aperture system for a CT scanner having a rotating source of radiation and a detector array including a series of stationary radiation detectors at least partially encircling the path of the source in the same plane, comprising:
  a radiation blocking body having at least one radiation passing aperture mounted for rotation about the source; and
  drive means for causing counter-rotation of said body about the source as the source rotates.

42. The system of claim 41, wherein said drive means includes means for causing a fixed amount of rotation of said body in the opposite direction for each angular unit of rotation of the source.

43. The system of claim 42, wherein said drive means includes mechanical drive means for causing said counterrotation powered by the rotation of the source itself.

44. The system of claim 43, wherein said mechanical drive means includes a set of wheels making driving contact with each other.

45. The system of claim 44, wherein said wheels are gears.

46. The system of claim 45, wherein said gears provide a gear reduction ratio of 1 to −0.60 of the source rotation to the rotation of said body about the source.

47. The system of claim 46, wherein said gears comprise an epicyclic gear train including a planetary gear concentric with said source and moving therewith to which said body is fixed, a stationary ring-shaped sun gear concentric to the scan circle, a compound drive gear consisting of a first gear engaging the sun gear and a second gear fixed to the first gear engaging the planetary gear.

48. The system of claim 47, wherein said epicyclic gear train provides a gear reduction ratio of 1 to −0.60 of the source rotation to the rotation of said body about the source.

49. The system of claim 48, wherein the ratio of the number of teeth on the sun gear to the number of teeth on the first compound gear multiplied by the ratio of the number of teeth on the second compound gear to the number of teeth on the planetary gear is 0.60.

50. The system of claim 49, wherein the detectors are all the same distance from the center of the scan circle 1.48 times the radius of the source path.

51. The system of claim 50, wherein the source is located at a distance of 24.3" from the center and the detectors are located 36.0" from the center.

* * * * *

UNITED STATES PATENT AND TRADEMARK OFFICE
CERTIFICATE OF CORRECTION

PATENT NO. : 4,190,773
DATED : February 26, 1980
INVENTOR(S) : Arthur B. Braden et al It is certified that error appears in the above—identified patent and that said Letters Patent is hereby corrected as shown below:

In the patent heading, the following patent assignment data is added following the line identified as [76] Inventor:

Assignee: Ohio-Nuclear, Inc.
                 Solon, Ohio

Signed and Sealed this

Twelfth Day of August 1980

[SEAL]

Attest:

SIDNEY A. DIAMOND

Attesting Officer     Commissioner of Patents and Trademarks